(12) United States Patent
Ashim et al.

(10) Patent No.: US 8,833,562 B2
(45) Date of Patent: Sep. 16, 2014

(54) FLOAT-SINK METHOD AND APPARATUS TO DETERMINE BENEFICIATION PROSPECTS OF MINERALS

(75) Inventors: Kumar Mukherjee Ashim, Jamshedpur (IN); Barada Kanta Mishra, Jamshedpur (IN)

(73) Assignee: Tata Steel Limited, Jamshedpur (IN)

( * ) Notice: Subject to any disclaimer, the term of this patent is extended or adjusted under 35 U.S.C. 154(b) by 47 days.

(21) Appl. No.: 13/513,732

(22) PCT Filed: Nov. 15, 2010

(86) PCT No.: PCT/IN2010/000741
§ 371 (c)(1),
(2), (4) Date: Aug. 16, 2012

(87) PCT Pub. No.: WO2011/061757
PCT Pub. Date: May 26, 2011

(65) Prior Publication Data
US 2012/0305453 A1    Dec. 6, 2012

(30) Foreign Application Priority Data

Nov. 18, 2009   (IN) .......................... 1368/KOL/2009

(51) Int. Cl.
*B03B 7/00*    (2006.01)
(52) U.S. Cl.
USPC .............................. 209/13; 209/17; 209/44.1
(58) Field of Classification Search
USPC ...................................... 209/13, 17, 44, 44.1
See application file for complete search history.

(56) References Cited

U.S. PATENT DOCUMENTS

| 2,319,394 | A | * | 5/1943 | Erickson | 241/20 |
| 2,330,479 | A | * | 9/1943 | Erickson | 241/20 |
| 3,696,923 | A | * | 10/1972 | Miller | 209/17 |
| 5,314,124 | A | * | 5/1994 | Kindig | 241/20 |
| 5,348,160 | A | * | 9/1994 | Kindig | 209/17 |
| 6,666,335 | B1 | * | 12/2003 | Bradley et al. | 209/3 |
| 6,742,656 | B2 | * | 6/2004 | Watters et al. | 209/2 |

FOREIGN PATENT DOCUMENTS

| CN | 201043946 Y | 4/2008 |
| DE | 29 23 842 A | 12/1980 |
| DE | 36 39 044 C1 | 6/1988 |
| DE | 101 27 935 A1 | 1/2002 |
| WO | 2008/061320 A1 | 5/2008 |

* cited by examiner

*Primary Examiner* — David H Bollinger
(74) *Attorney, Agent, or Firm* — The Webb Law Firm

(57) ABSTRACT

A method for separating particles of different specific gravity from a sized ore feed, wherein the ore can be coal, metallic, non-metallic and mineral ores. The method particles from the ore are sieved to obtain size fractions of different particle size ranges, after which a load of particles of a size fraction are placed in a container and fluidized by passing a fluid flow through the load of particles. By lowering the flow velocity of the fluid through the load the particles are deposited in the container in one or more layers depending on the specific gravity of each of the particles, after which the deposited particles are separated in portions of different specific gravity. The portions represent different ore content of the particles in each portion on basis of which the theoretical yield of the ore can be determined. The invention provides an apparatus to carry out the method.

26 Claims, 3 Drawing Sheets

FLOAT-SINK METHOD AND APPARATUS TO DETERMINE BENEFICIATION PROSPECTS OF MINERALS

BACKGROUND OF THE INVENTION

1. Filed of the Invention

The present invention relates to a method and apparatus to determine the theoretical yield of the coal and minerals concentrate at different impurity levels. More particularly, the invention relates to a method and a float-sink apparatus adaptable to determine beneficiation prospects of coal, metallic, non-metallic ore and, industrial minerals in a beneficiation process.

2. Description of the Related Art

In case of coal or any other mineral, beneficiation prospect of the feed is evaluated by graphically developing a curve which indicates theoretical yield values of the concentrate at different impurities level. The theoretical yield values are considered as the maximum achievable yield at the corresponding impurities level in the concentrate. This is a valuable information as it directly shows the liberation status of the feed, concentrate yield versus grade relation and loss of values in the reject. The theoretical yield values are compared with the actual yield values of the plant or machine to arrive at the efficiency of the plant or the machine. The general expression for the efficiency is $=[-(\text{Actual yield})/\text{Theoretical Yield})]*100$.

Theoretical yield for coal is determined through a series of float-sink tests. The process starts with the preparation of heavy media liquids of specific gravity 1.3 to 2.2 with intervals of 0.1. These liquids are prepared by mixing benzene, tetrachloro-ethylene and, bromoform in different proportions. The float-sink tests are conducted with feed coal at size ranges identical to the size ranges fed in the washery. The coal is first tested on 1.3 specific gravity liquid and the float obtained is the purest coal in the feed. The sink is again treated on the next higher specific gravity liquid which is 1.4. The process continues till float and sink fractions are obtained from 2.2 specific gravity liquid. At the end of the process along with one sink fraction, float fractions from each specific gravity liquids are generated. All these fractions are then analysed for their ash content. Ash content of the float from 1.3 specific gravity liquid is minimum which increases successively for the rest of the float fractions and the lone sink fraction shows the highest ash content. This trend is universal for coal as the specific gravity of ash containing minerals is higher than pure coal matter. These set of data is used to generate the theoretical yield-ash curve of washed (clean) coal and is often described as the washability curve. Although in case of coal the process described hereinabove is well established, however in case of minerals such process is not that established as the liquids used for float-sink tests of coal cannot be used in minerals as the specific gravity of minerals are much higher than that of coal. In case of minerals, the application of float-sink tests is industry specific and often not conclusive by itself. For example, the known beneficiation methods followed in beach sand minerals involves testing of the feed in bromoform (a liquid of specific gravity 2.88). The liquid separates all heavy minerals from the silicates. The heavy minerals are then washed with acetylene prior to semi quantitative estimation of minerals through microscopical method.

In iron ore industry two different types of methods are being used, but none of them is self sufficient. In the first method, the atomised Ferro-silicon is mixed in different proportions with water to create suspended solutions of solid which could provide mixtures of different specific gravity. Thereafter, the feed iron ore is tested in the mixtures having low to high specific gravity. The float fractions and the lone sink fraction are then chemically analysed for their iron content. In case of minerals float fraction contains more of impurities and the sink represents the purest form of minerals. The known method is not self sufficient because of the difficulties in preparation of high specific gravity medium through this prior art method. Therefore, this known method fails to allow extension of the theoretical yield-grade curve to a desired grade concentrate level.

In the second method, three separate specific gravity liquids namely; ethylene bromide, di-iodomethane and clarici solution of specific gravity 2.96, 3.30 and 4.03 respectively, are used in a sequence. These liquids are immiscible to one another and thus, liquids of intermediate specific gravity cannot be generated by mixing which remains the major disadvantages of this known method. The second method generates a few discrete theoretical yield values corresponding to concentrate grade, instead of a continuous curve and thereby the purpose of the tests is often partly defeated. Furthermore, a liquid of specific gravity higher than 4.03 is often required to separate iron concentrate of desired grade from a poorly liberated ore. In such cases, the theoretical yield of the concentrate cannot be obtained from this test. In addition, the float-sink analysis is carried out with organic liquids which are not environment friendly and often hazardous. Most of these liquids are costly and not readily available in the market. Owing to these disadvantages, the float-sink tests are not a regular practice in mineral sector resulting to either yield loss or deterioration of the concentrate quality in the plant.

SUMMARY OF THE INVETION

It is therefore an objective of the invention to provide a method to easily and reliably determine the theoretical yield of coal as well as for metallic, non-metallic and mineral ores.

It is a further objective of the invention to provide a method to separate portions of a particle size fraction with different specific gravity for coal as well as for metallic, non-metallic and mineral ores.

It is a further objective of the invention to provide a method which allows to separate easily and reliably portions of a particle size fraction with different specific gravity for coal as well as for metallic, non-metallic and mineral ores.

It is a further objective of the invention to provide an apparatus to separate portions of a particle size fraction with different specific gravity for coal as well as for metallic, non-metallic and mineral ores.

It is still a further objective of the invention to provide an apparatus with which portions of a particle size fraction with different specific gravity for coal as well as for metallic, non-metallic and mineral ores can be separated easily and against low costs.

According to a first aspect of the invention one or more of the above objectives are realized by providing a method for separating particles of different specific gravity from a sized ore feed, the method comprising the steps of:
 a) sieving particles to obtain size fractions of different particle size ranges,
 b) placing a load of particles of a size fraction in a container,
 c) fluidizing the particles by passing a fluid flow through the load of particles,
 d) lowering the flow velocity of the fluid through the load of particles to let the particles deposit in the container, e) dividing the deposited particles in the container in separate portions.

In the present description the term "ore" comprises coal as well as metallic, non-metallic and mineral ores. With the term "sized ore feed" the fraction of a feed of coal or other ore is meant that remains within the defined maximum and the minimum size.

With the present method the particles should be about equal size in order to be able to separate particles having different specific gravity. The position of particles during complete fluidization depends on the force balance of three important forces acting on the particles. These forces are weight, buoyancy and, drag. Particles of same size include same buoyancy and drag assuming an uniform voidage around the particles, wherein voidage is the fraction of the bed not filled with particles. However, weight of these particles differs which is the function of the respective specific gravity of these particles. Therefore, depending on the specific gravity these particles attain their terminal velocity, wherein the terminal velocity is the constant velocity or settling velocity of a particle due to the restraining force exerted by the fluid through which it is moving. The heaviest category of particles show highest terminal velocity and reaches to the bottom of the fluidization column earlier than other category of particles. The next category of heavier particles follows the trend and forms the next layer. The process continues and layers are formed with successive layers each lighter than the previous. However, these layers are not very stable and some degree of mixing cannot be avoided, as these particles realize more drag due to less voidage around them as soon as they tend to settle to the bottom. With this increased drag, the particles again get partially fluidized and allow the fluid to flow through the bed. Therefore, these layers are dynamic in nature and a partial mixing is expected.

During fluidization, there is another possibility for example, some of the particles tend to remain in the fluidized state at applied superficial-fluid velocity as these particles attain zero terminal velocity. To allow these particles to segregate, the superficial-fluid velocity is lowered. Lowering of the fluid velocity is either done in a continuous manner or stepwise. The process is continued till all fluidized particles are segregated and settled to the bottom.

In order to get a good segregation of particles in different size fractions it is provided that for a separated portion the steps b)-c) are repeated one or more times. Every load of particles after having settled after fluidisation may be separated in two or more portions. However, since some mixing will occur in the settled particles it will generally not possible to separate the settled particles in sharply defined layers. For that reason the settled particles are preferably divided in only a limited number of portions, for instance two portions, a first portion with particles with a greater specific gravity and a second portion with particles with a lesser specific gravity. The method is then repeated one or more times for each separated portion. In this way a good separation may be obtained on basis of which a reliable determination of the theoretical yield of the ore can be obtained.

According to a further aspect of the invention it is provided that of the four portions resulting after the second fluidization, depositing and dividing of the first and second portions resulting from the first fluidization, depositing and dividing, a third fluidization and depositing is carried out for the portions with respectively the highest and lowest specific gravity and each is divided in two further portions.

With this further step the particles are divided in 6 portions of different specific gravity, 4 portions resulting from the previous portions with the highest and lowest specific gravity and 2 portions with intermediate specific gravity resulting from the previous fluidisation and depositing.

According to a further aspect of the invention the two portions of intermediate specific gravity resulting from the second fluidization are first mixed after which a third fluidization, depositing is carried out for the mixed portion and divided in two further portions. This mixing and fluidisation step is carried out to get a better segregation of particles of different specific gravity in two portions.

According to a further aspect of the invention said two further portions resulting from fluidizing, depositing and dividing of the portions of intermediate specific gravity are subjected to a fourth fluidization, depositing and dividing, and wherein the intermediate portions of the four resulting portions are mixed and subjected to a fifth fluidizing, depositing and dividing in two further portions.

By carrying out these fourth and fifth fluidizing, depositing and dividing step 4 well separated portions are obtained and all together 8 well separated portions of different specific gravity are obtained of particles of one size fraction of the feed. By carrying out the same steps for every size fraction of the feed the feed will be separated in a sufficient number of portions to be able to determine the theoretical yield of the ore.

Depending on the variation in specific gravity within a size fraction the number of portions needed could be different for different ores. The above separation in 8 portions of different specific gravity for each size fraction works very well with coal. For other ores the number of portions of different specific gravity required for determining the theoretical yield of the ore could be less or more and is to be determined for each specific ore or load of a specific ore.

With the fluidisation of the particles the flow velocity of the liquid through the fluidisation container is such that the total volume of particles and voids between the particles is between 1.5-3.0 times the volume of the particles. Preferably, the total volume of particles and voids between the particles is between 1.5-2.2 times the volume of the particles. With a ratio of 2.0 the fluidisation is defined to be a complete fluidisation.

The flow velocity of the fluid is lowered from a maximum velocity either in a continuously manner or stepwise, wherein the particles will either deposit with a gradual transition from a higher specific gravity to a lower specific gravity or in a more stepwise transition.

Preferably the fluid used is water. However, while water will work very well with coal, for ores with higher specific gravity other fluids with a higher specific gravity than water can be used.

According to a further aspect of the invention the difference in size of the particles in a particle size range varies from 0.5-3.0 mm, preferably from 0.5-2.0 mm and even more preferably from 0.5-1.0 mm. In order to be able to get good results from the fluidisation, depositing and dividing of the particles in different portion of specific gravity it is necessary to sieve the ore feed in size fractions within a narrow diameter range. With a wide range of particle sizes in a sized ore feed this could mean that a large number of size fractions have to be prepared and be subjected to the method. Instead of applying the method on each and every size fraction, the method could also be applied on a number of size fractions that are taken from the whole size range in such a manner that the selected size fractions form a representative selection of the feed.

According to a further aspect the invention also provides a method to determine the theoretical yield of a sized ore feed, wherein the sized ore feed is divided in size fractions of different particle size ranges and each size fraction is divided in portions of different specific gravity according the above describes method after which the ore content of each portion of each size fraction is determined.

To determine the theoretical yield of coal the ash content of each portion of a specific gravity and of a specific size range is determined. This set of data is used to generate the theoretical yield-ash curve of washed (clean) coal and is often referred to as the washability curve.

If the method is applied to iron ore the iron content of the iron ore is determined by chemical analysis of each portion of a specific gravity and wherein the obtained data is used to determine the theoretical yield.

The invention also provides an apparatus to carry out the method, wherein the apparatus for fluidizing particles comprises a fluidisation container provided with a fluid supply connected to the bottom of the container, a fluid outlet at a distance above the bottom part of the container, means to control the superficial flow velocity of the fluid through the container and a particle container which fits in or connects to the fluidisation container.

In order to get a stable fluidised bed of particles it is important to provide a homogenized flow of fluid entering the fluidisation container. Accordingly means are provided to homogenize the flow the fluid before entering the fluidization container. These means may consist of a chamber at the bottom of the fluidization container with means to minimize any turbulence in the flow of the fluid. The homogenisation chamber is provided with a fine mesh at the transition to the fluidisation container in order to prevent that fine particles from the fluidization chamber might enter the homogenisation chamber.

Although the fluidisation container may have any suitable shape it is preferred that the fluidisation container is an elongated cylindrical container.

The load of particles of a size fraction are preferably placed inside the fluidisation container by means of a particle container. Such a particle container not only make it easier to place the particles in the container, but even more important with the particle container the segregated settled particles obtained by applying the method can easily be removed from the fluidisation container without the danger of disrupting the segregated particle layers in the particle container. Moreover, the particle container can be designed such that after removing the particle container from the fluidisation container the load of particles can easily be separated in two ore more portions. For instance by means of a particle container that is made up of annular shaped parts which can be separated by sliding the parts from each other. In order to keep the particles in the particle container and to let the fluid pass from the homogenisation chamber into the fluidization container the bottom part of the particle container is provided with a mesh.

The means to control the flow velocity of the fluid through the fluidization container comprises a fluid pump in a supply line connected to a fluid supply and the fluidisation container. According to a further embodiment the fluid supply is a fluid container holding the fluid. With a fluid container the apparatus is not dependent on an external fluid supply such as the public water supply system. The advantage is that a larger flow can be generated than possible with the public water supply system and that other fluids than water can be used. A further advantage is that the apparatus can be set-up as a portable or mobile system and be used in the field.

By providing a return line provided with a controllable valve which connects to the supply line between the fluid pump and the fluidisation container the velocity of the flow can be controlled by controlling the valve in the return line. The controllable valve can also be used in combination with a controllable fluid pump to enable fine adjustment of the flow velocity. The apparatus is further provided with a fluid velocity meter in the fluid supply line between the return line and the fluidisation container to be able to closely control the flow velocity of the fluid.

Further a return line is provided between the fluid outlet of the fluidization container and the fluid container. This allows to perform the method with a limited amount of water or other fluid and also allows to set-up a portable or a mobile system.

In the return line filtering means are provided between the fluid outlet of the fluidization container and the fluid container to prevent particles of any kind entering the fluid container.

The fluidisation container is provided with sample outlets spaced along the height of the fluidisation container which allows to take samples of particles of low specific gravity.

BRIEF DESCRIPTION OF THE DRAWINGS

The invention is further elucidated on hand of the non-limiting example shown in the drawing, wherein.

DETAILED DESCRIPTION OF THE PREFERRED EMBODIMENTS

The prior art discussion establishes that the process of particle segregation based on their specific gravity through fluidization is possible for particle of similar size and shape. However, in practice, feed containing particles of same size and shape is not achievable although a process can be designed to prepare feed close to the theoretical assumption. According to the invention, the feed is prepared by screening a feed of narrow ranged sized fractions and then each of these size fractions is separately tested in the fluidization apparatus.

Figure 1A:
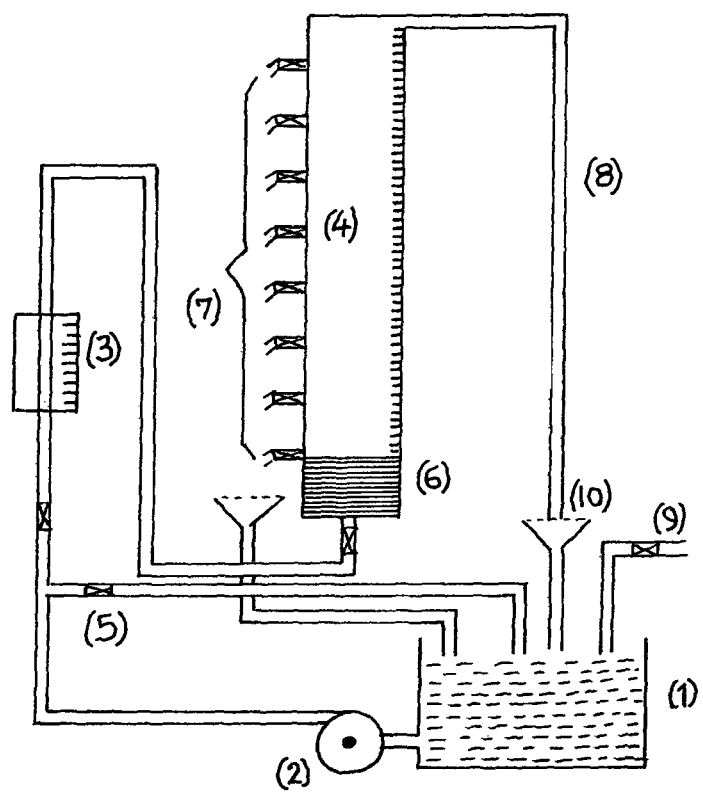
FIG. 1(a) shows a schematic diagram of the apparatus according to the invention.
Figure 1B:
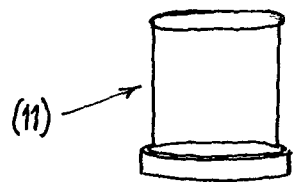
FIG. 1(b) shows a schematic diagram of a particle container to be placed inside the apparatus of FIG. 1(a) during the test.

As shown in FIG. 1b, a particle container 11 holds particles for which the fluidization test is to be carried out. On completion of the test, this particle container 11 again holds all the settled particles. The particle container 11 is taken out after the fluidization test from the fluidization column 4. With a segregation in two portions the upper half of particle container 11 contains lighter particles and the bottom half contains the heavier particles. These two portions are separated after each cycle of operation.

Figure 2:
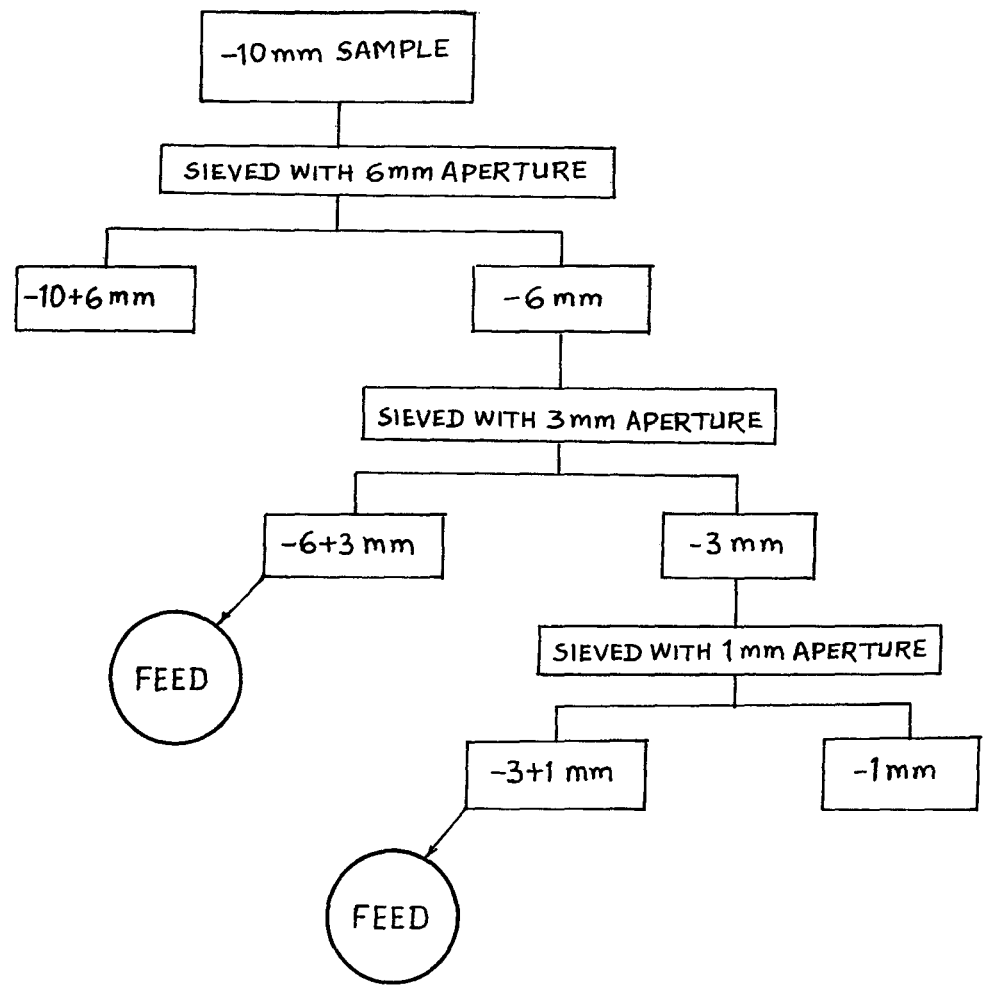
FIG. 2 schematically shows a feed preparation before fluidisation of the different size fractions of the feed in the apparatus.

Now FIG. 2 shows that the feed is prepared from −10.0 mm size fraction. The main purpose of the feed preparation step is to generate closed size fractions from the feed. Each of these size fractions is then separately tested in the machine to generate relationship between theoretical yields and concentrate grade for each size fraction as well as for the entire feed.

Figure 3:
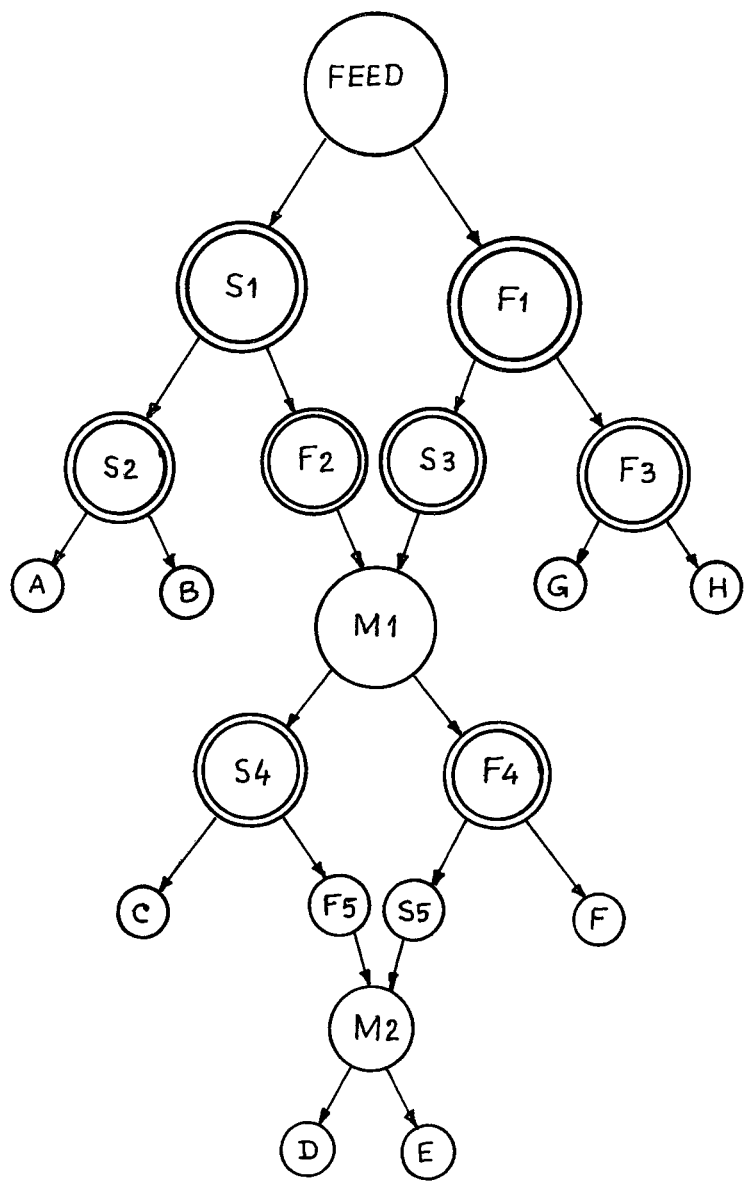
FIG. 3 schematically shows a step adopted for separating fractions of different specific gravity material from a sized ore feed.

FIG. 3 further shows that the sink is indicated by the numeral S whereas the float is indicated by the numeral F. It may be noted that these set of operation segregate the pure heavy and light material at the initial phase and then the intermediate fractions are repeatedly fluidized so as to ensure a complete segregation of lighter and heavier particles from the near gravity fractions.

As shown in FIG. 2, the feed particles are screened to close size range using manual/mechanical sieves. Each of these size fractions is tested separately to find out the theoretical yield-grade relation for each size fractions. One such size fraction is transferred to particle container 11 (11) and the total particle volume is maintained little less than the cylinder volume. The fluidization column (4) having a plurality of sample collection ports (7). The particle container 11 filled with particles is placed at the bottom of the fluidization column (4). Flanges (not shown in the drawing) at the bottom of the fluidization column (4), the small cylinder(11) and, a homogenization chamber (6) are tightened with screws.

The homogenization chamber and the fluidization column are separated by a first fine mesh screen, and a second fine mesh screen is provided between the fluidization column and an upper outlet of the fluidization column to prevent elutriation of finer particle.

A water pump (2) in the fluid supply line to the fluidisation column 4 is then switche on with a by pass valve full open and this allows water to flow through the fluidization colum(4) at a lower superficial water velocity. In the supply line to the fluidisation column 4 a flow meter 3 such as a rotometer is provided. An overflow line (8) which otherwise is connected to a fluid container (1) is placed in the drain at the initial stage of the test and a fresh water line (9) to the fluid container (1) is also kept full open. Draining of turbid water through the overflow line (8) is allowed to continue for some time so that slime/very fine particles adhering to the coarse particles are drained. Once the water inside the fluidization column (4) is reasonably clear the overflow line (8) is again placed on the fluid container and a valve of the fresh water line (9) that supplies water to the fluid container (1) is completely closed. The circuit is then a closed circuit. To prevent that very fine particles would end up in fluid container 1 filtering means 10 are provided in overflow line 8.

In the next stage, the superficial water velocity in the fluidization column (4) is increased in steps by manipulating the valve placed in a bypass line (5). The superficial water velocity is increased till the fluidized bed attains a volume which is almost twice of the particle volume. For any particular particle type a mark is inserted on the fluidization column (4) before commencement of the test. The superficial water velocity is maintained for few minutes in this state to allow the particles to segregate. In the subsequent stages, the superficial water velocity is reduced in steps which causes all particles to settle inside the small column as per their density with the lighter particles settling at the top. The flow velocity of the water is finally reduced to a flow velocity of zero. The valve in the bypass line 5 is again fully opened and then the pump (2) is switched off. Water in the fluidization column (4) is drained out by opening the valve placed just below the homogenization chamber (6).

The particle container 11 in which particles have settled is then taken out and placed upside down on a steel plate. The particle container 11 is then lifted a bit and dragged over the plate so that particles come out to form the bed. The particle bed is then divided into two parts i.e., the lighter and heavier fraction. The process is repeated several times to generate sufficient quantity of light and heavy fraction. Following the steps of FIG. 3 fluidization tests are carried out with these two fractions to generate eight different specific gravity fractions. In case of iron ore feed, each of these fraction is then weighted and chemically analysed for its iron, alumina and silica content. Other chemical components may be analysed as per the feed and the beneficiation requirement. With these data the theoretical yield and grade (with respect to total iron, alumina and silica) is plotted. Similar curve is generated for other metallic, non-metallic minerals and, coal.

The invention provides an improved float-sink apparatus, which uses the fundamental principle of fluidization in separating particles of different specific gravity when the feed is prepared with closed size particles.

According to the inventive method water is used as opposed to the prior art method in which chemicals of different specific gravities are used for separating particle. Therefore, the method of this invention is environment friendly, not hazardous and less costly.

The inventive method can be used for the feed with wide size distribution and also for larger-volume of feed since, the method does not require using costly and hazardous chemicals.

The present method is useful for coal, metallic and, non-metallic ores and industrial minerals. For the existing methods, for metallic and non-metallic minerals, a theoretical yield-grade relationship can not be based reliably on a float-sink analysis, due to limitation in the availability of various types of specific gravity liquids. Thus, a theoretical yield curve has to be drawn by interpolation of only a few data points, which often mislead the operator. In contrast thereto, the inventive method is enabled to generate a large number of points and provides more reliable data.

The inventive method is adaptable to all coal, metallic, non-metallic ore and industrial mineral mines and beneficiation processes. The operation is easy, quick and does not demand a lot of skill.

The improved apparatus provided by the invention, is a portable or a mobile unit and hence can be used at the mine site or in the beneficial plant.

We claim

1. A method for separating particles of different specific gravity from a sized ore feed, the method comprising the steps of:
    sieving particles to obtain size fractions of different particle size ranges;
    placing a load of particles of a size fraction in a container;
    fluidizing the particles by passing a fluid flow through the load of particles;
    lowering the flow velocity of the fluid through the load of particles to let the particles deposit in the container; and
    dividing the deposited particles in the container in separate portions.

2. The method according to claim 1, wherein for a separated portion the above steps are repeated one or more times.

3. The method according to claim 1, wherein the deposited particles are divided in two portions, a first portion with particles with a greater specific gravity and a second portion with particles with a lesser specific gravity.

4. The method according to claim 3, wherein four portions result after a second fluidization, and wherein depositing and dividing of the first and second portions result from the first fluidization, depositing and dividing, and wherein a third fluidization and depositing is carried out for the portions with respectively the highest and lowest specific gravity and each is divided in two further portions.

5. The method according to claim 4, wherein the two portions of intermediate specific gravity resulting from the second fluidization are first mixed after which a third fluidization, depositing is carried out for the mixed portion and divided in two further portions.

6. The method according to claim 5, wherein said two further portions resulting from fluidizing, depositing and dividing of the portions of intermediate specific gravity are subjected to a fourth fluidization, depositing and dividing, and wherein the intermediate portions of the four resulting portions are mixed and subjected to a fifth fluidizing, depositing and dividing in two further portions.

7. The method according to claim 1, wherein the flow velocity of the fluid is controlled to obtain a fluidized particle bed with a volume between 1.5-3 times the volume of the load of particles.

8. The method according to claim 7, wherein the flow velocity of the fluid is controlled to obtain a fluidized particle bed with a volume between 1.5-2.2 times the volume of the load of particles.

9. The method according to claim 1, wherein the flow velocity of the fluid is decreased stepwise.

10. The method according to claim 1, wherein the fluid is water.

11. The method according to claim 1, wherein the difference in size in a particle size range varies from 0.5-3.0 mm.

12. A method to determine the yield of a sized ore feed, wherein the sized ore feed is divided in size fractions of different particle size ranges and each size fraction is divided in portions of different specific gravity according to claim 1 after which the ore content of each portion of each size fraction is determined.

13. The method according to claim 12, wherein each size fraction is divided in 8 portions of different specific gravity.

14. The method according to claim 12, wherein the ore is coal and the coal content of the coal is determined by determining the ash content of each portion.

15. The method according to claim 12, wherein the ore is iron ore and wherein the iron content of iron ore is determined by chemical analysis of each portion.

16. The method according to claim 1, wherein the difference in size in a particle size range varies from 0.5-2.0 mm.

17. The method according to claim 1, wherein the difference in size in a particle size range varies from 0.5-1.0 mm.

18. An apparatus for fluidizing particles comprising:
a fluidization container provided with a fluid supply connected to the bottom of the container, wherein the fluidization container is provided with sample outlets spaced along the height of the fluidization container;
a fluid outlet at a distance above the bottom part of the container,
a flow velocity controller for controlling the flow velocity of the fluid through the container;
a particle container which fits in or connects to the fluidization container; and
a flow homogenizer provided to homogenize the flow of the fluid before entering the fluidization container.

19. The apparatus according to claim 18, wherein the fluidization container is an elongated cylindrical container.

20. The apparatus according to claim 18, wherein the bottom part of the particle container comprises a mesh.

21. The apparatus according to claim 18, wherein the flow velocity controller comprises a fluid pump in a supply line connected to a fluid supply and the fluidization container.

22. The apparatus according to claim 21, wherein the fluid supply is a fluid container holding the fluid.

23. The apparatus according to claim 22, wherein a return line provided with a controllable valve is connected to the supply line between the fluid pump and the fluidization container.

24. The apparatus according to claim 23, wherein a fluid flow meter is provided in the fluid supply line before the fluidization container.

25. The apparatus according to claim 18, wherein a return line is provided between the fluid outlet of the fluidization container and the fluid container.

26. The apparatus according to claim 25, wherein a filter is provided in the return line between the fluid outlet of the fluidization container and the fluid container.

* * * * *